United States Patent
Leem et al.

(10) Patent No.: US 9,939,388 B2
(45) Date of Patent: Apr. 10, 2018

(54) APPARATUS FOR INSPECTING WAFER

(71) Applicant: Samsung Electronics Co., Ltd., Suwon-si, Gyeonggi-do (KR)

(72) Inventors: Choon-Shik Leem, Seoul (KR); Woo-Jin Jung, Seoul (KR); Chung-Sam Jun, Suwon-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 31 days.

(21) Appl. No.: 15/183,003

(22) Filed: Jun. 15, 2016

(65) Prior Publication Data

US 2017/0115233 A1    Apr. 27, 2017

(30) Foreign Application Priority Data

Oct. 22, 2015 (KR) .................. 10-2015-0147321

(51) Int. Cl.
| | | |
|---|---|---|
| *G01N 21/00* | (2006.01) | |
| *G01N 21/88* | (2006.01) | |
| *H01L 21/67* | (2006.01) | |
| *G01N 21/95* | (2006.01) | |

(52) U.S. Cl.
CPC ..... *G01N 21/8851* (2013.01); *G01N 21/9501* (2013.01); *H01L 21/67288* (2013.01); *G01N 2021/8887* (2013.01)

(58) Field of Classification Search
CPC ........... G01N 21/8851; G01N 21/9501; G01N 27/20; G01N 27/82; G01N 2021/8887; H01L 21/67288; G06T 7/0004
USPC .......................................... 356/237.1–237.5
See application file for complete search history.

(56) References Cited

U.S. PATENT DOCUMENTS

| | | | |
|---|---|---|---|
| 5,646,870 A * | 7/1997 | Krivokapic | G03F 7/70625 |
| | | | 700/117 |
| 6,724,005 B2 | 4/2004 | Tokumoto | |
| 7,330,260 B2 | 2/2008 | Nicolaides et al. | |
| 7,813,539 B2 * | 10/2010 | Shibuya | G06T 7/0004 |
| | | | 382/141 |
| 7,902,485 B2 | 3/2011 | Jyousaka et al. | |
| 8,041,525 B2 | 10/2011 | Kondo et al. | |
| 8,116,556 B2 * | 2/2012 | Shibuya | G06T 7/0004 |
| | | | 382/141 |
| 8,117,001 B2 | 2/2012 | Lee et al. | |
| 8,238,645 B2 | 8/2012 | Postolov et al. | |
| 2009/0161097 A1 * | 6/2009 | Friedrich | G01N 21/9501 |
| | | | 356/237.5 |
| 2012/0218533 A1 | 8/2012 | Lyulina et al. | |

(Continued)

FOREIGN PATENT DOCUMENTS

KR    2009-0071732 A    7/2009

*Primary Examiner* — Hoa Pham
(74) *Attorney, Agent, or Firm* — Harness, Dickey & Pierce, P.L.C.

(57) ABSTRACT

A wafer inspection apparatus including a derivation unit configured to derive a first polar coordinate set and a second polar coordinate set using a latin hypercube sampling, the first and second polar coordinate sets not overlapping each other, an inspection unit configured to perform defect inspections of a plurality of wafers using the first and second polar coordinate sets, a support unit configured to support the wafers, and an calculation unit configured to combine a defect inspection result using the first polar coordinate set with a defect inspection result using the second polar coordinate set may be provided.

17 Claims, 17 Drawing Sheets

(56) References Cited

U.S. PATENT DOCUMENTS

2014/0375988 A1* 12/2014 Ito .................. G01B 11/303
356/237.5
2016/0351455 A1* 12/2016 Jung .................. H01L 22/12

* cited by examiner

163

260

271

272

270

APPARATUS FOR INSPECTING WAFER

This application claims priority under 35 U.S.C. § 119 to Korean Patent Application No. 10-2015-0147321, filed on Oct. 22, 2015 in the Korean Intellectual Property Office, the disclosure of which is incorporated herein by reference in its entirety.

BACKGROUND

1. Technical Field

Example embodiments of the present inventive concepts relate to apparatuses for inspecting a wafer.

2. Description of the Related Art

Manufacturing processes of a semiconductor device are seriously affected by contamination (e.g., particles of several micrometers). Thus, various efforts have been maded for managing and removing the contamination sources have been constantly.

While going through the respective processes, surface defects due to various causes may occur on a surface of a wafer, and/or a surface contamination due to particles and the like may occur. Fabricating a semiconductor element on such defective and/or contaminated wafers is challenging. Thus, defective and/or contaminated wafers have been screened out using a surface inspection process.

Various cleaning processes and the like are also performed when producing a wafer by growing an ingot and cutting the grown ingot. Thus, scanning (checking) the number of particles that exist on the wafer surface after completion of such a cleaning process is desired. Based on the scanned results, defective products may be prevented from being shipped.

SUMMARY

Some example embodiments of the present inventive concepts provide wafer inspection apparatuses that monitor defects of the wafer using polar coordinate sets, which are derived by a latin hypercube sampling.

Some example embodiments of the present inventive concepts provide wafer inspection apparatuses that monitor defects of the wafer using cartesian coordinate sets, which are derived by the latin hypercube sampling.

According to an example embodiment of the present inventive concepts, a wafer inspection apparatus includes a derivation unit configured to derive a first polar coordinate set and a second polar coordinate set using a latin hypercube sampling, the first and second polar coordinate set not overlapping each other, an inspection unit configured to perform defect inspections of a plurality of wafers using the first and second polar coordinate sets, a support unit configured to support the wafers, and an calculation unit configured to combine a defect inspection result using the first polar coordinate set with a defect inspection result using the second polar coordinate set. The first and second polar coordinate sets may be distributed over an entire region on a virtual wafer, and the first and second polar coordinate sets may be provided on a polar coordinate system that is made up of (1) a distance from an origin of the virtual wafer to the respective polar coordinates, and (2) an angle formed between a line connecting the origin of the virtual wafer with the respective polar coordinates and an X-axis.

According to an example embodiment of the present inventive concepts, a wafer inspection apparatus includes a derivation unit configured to derive, using a latin hypercube sampling, a first cartesian coordinate set, and a second cartesian coordinate set, the first and second cartesian coordinate sets not overlapping each other, an inspection unit configured to perform a defect inspection of a first wafer using the first cartesian coordinate set, and perform a defect inspection of a second wafer different from the first wafer using the second cartesian coordinate set, a support unit configured to support the first and second wafers, and an calculation unit configured to combine a defect inspection result of the first wafer with a defect inspection result of the second wafer. The first and second cartesian coordinate sets may be distributed over an entire region on the wafer, and the first and second cartesian coordinate sets may be provided on a cartesian coordinate system made up of an X-axis and a Y-axis.

According to an example embodiment of the present inventive concepts, a wafer inspection apparatus includes a memory having computer-readable instructions stored therein, and at least one processor configured to execute the computer-readable instructions to cause the wafer inspection apparatus to derive a plurality of select polar coordinate sets using a latin hypercube sampling, the select polar coordinate sets not overlapping one another, the select polar coordinate sets provided on a polar coordinate system and including (1) a distance from an origin of the wafer to the respective select polar coordinates, and (2) an angle formed between a line connecting the origin of the wafer with the respective select polar coordinates and an X-axis, inspect wafers for defects using the select polar coordinate sets, and combine and represent defect inspection results on a virtual wafer.

Example embodiments of the present inventive concepts are not limited thereto, and other aspects that have not been mentioned will become more apparent to one of ordinary skill in the art to which the present inventive concepts pertains by referencing the detailed description of the present inventive concepts given below.

BRIEF DESCRIPTION OF THE DRAWINGS

The above and other aspects and features of the present inventive concepts will become more apparent by describing in detail example embodiments thereof with reference to the attached drawings, in which.

DETAILED DESCRIPTION

Figure 1:
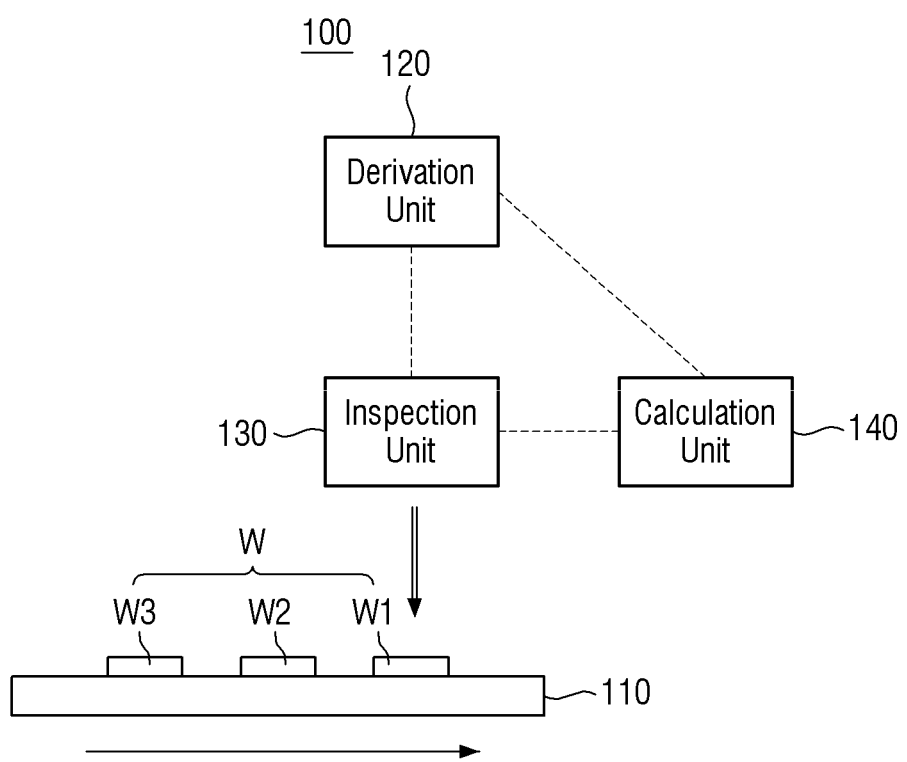
FIG. 1 is a diagram illustrating a wafer inspection apparatus according to an example embodiment of the present inventive concepts.

Various example embodiments of the present concepts will be described more fully hereinafter with reference to the accompanying drawings. Example embodiments may, however, be embodied in many different forms and should not be construed as limited to the example embodiments set forth herein. Rather, these example embodiments are merely provided so that this disclosure will be thorough and complete, and will fully convey the scope of example embodiments to those skilled in the art. In the drawings, the size and relative sizes of layers and regions may be exaggerated for clarity. Like reference numerals may refer to like elements throughout the accompanying drawings.

It will be understood that when an element or layer is referred to as being "on," "connected to", or "covered by" another element or layer, it can be directly on, connected to, or covered by the other element or layer or intervening elements or layers may be present. In addition, it will also be understood that when an element or layer is referred to as being "between" two elements or layers, it can be the only element or layer between the two elements or layers, or one or more intervening elements or layers may also be present. As used herein, the term "and/or" includes any and all combinations of one or more of the associated listed items. Further, when two or more elements or values are described as being substantially the same as or equal to each other, it is to be understood that the elements or values are identical to each other, indistinguishable from each other, or distinguishable from each other but functionally the same as each other as would be understood by a person having ordinary skill in the art.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

It will be understood that, although the terms first, second, etc. may be used herein to describe various elements, these elements should not be limited by these terms. These terms are only used to distinguish one element from another element. Thus, for example, a first element, a first component or a first section discussed below could be termed a second element, a second component or a second section without departing from the teachings of the present concepts.

The present concepts will be described with reference to perspective views, cross-sectional views, and/or plan views, in which example embodiments of the concepts are shown. Thus, the profile of an example view may be modified according to manufacturing techniques and/or allowances. That is, the example embodiments of the concepts are not intended to limit the scope of the present concepts but cover all changes and modifications that can be caused due to a change in manufacturing process. Thus, regions shown in the drawings are illustrated in schematic form and the shapes of the regions are presented simply by way of illustration and not as a limitation.

The terminology used herein is for the purpose of describing particular example embodiments only and is not intended to be limiting of example embodiments. As used herein, the singular forms "a," "an" and the are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

Hereinafter, a wafer inspection apparatus according to an example embodiment of the present inventive concepts will be described with reference to FIG. 1 to FIG. 5.

Figure 2:
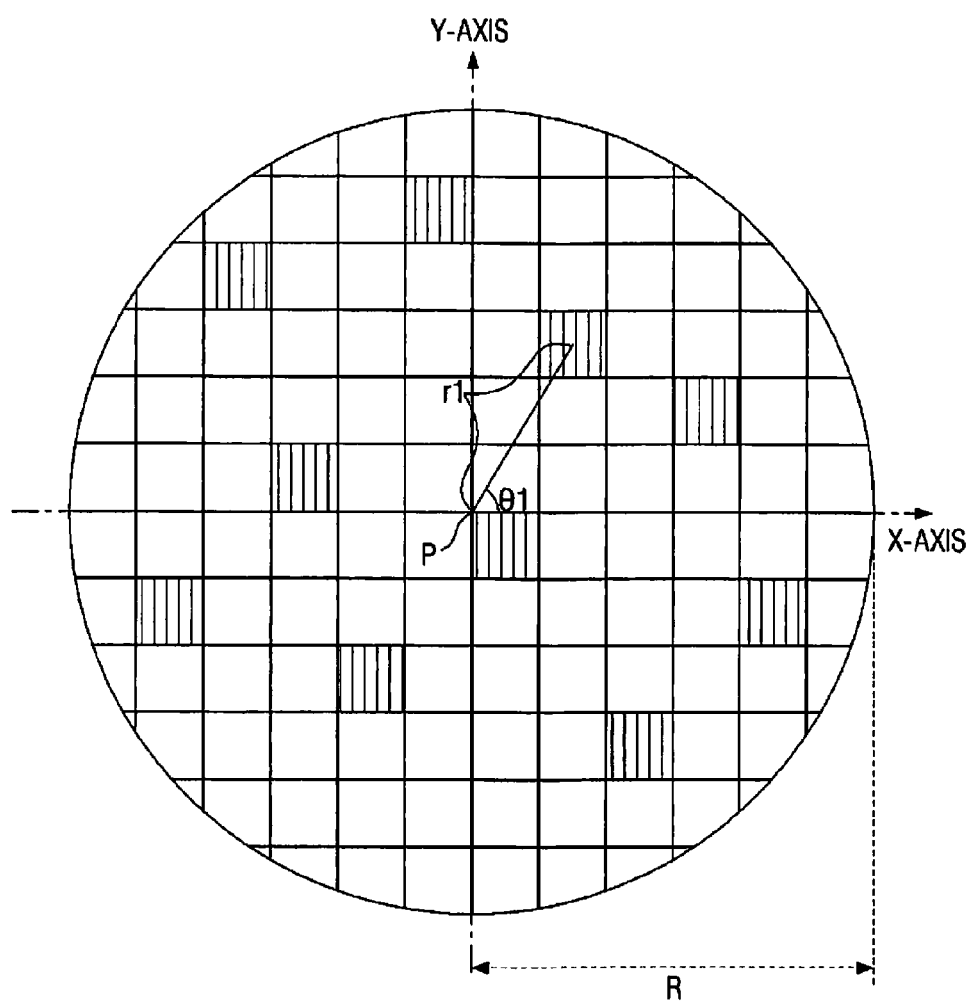
FIG. 2 to FIG. 4 are diagrams illustrating polar coordinate sets derived by the water inspection apparatus according to an example embodiment of the present inventive concepts.
Figure 3:
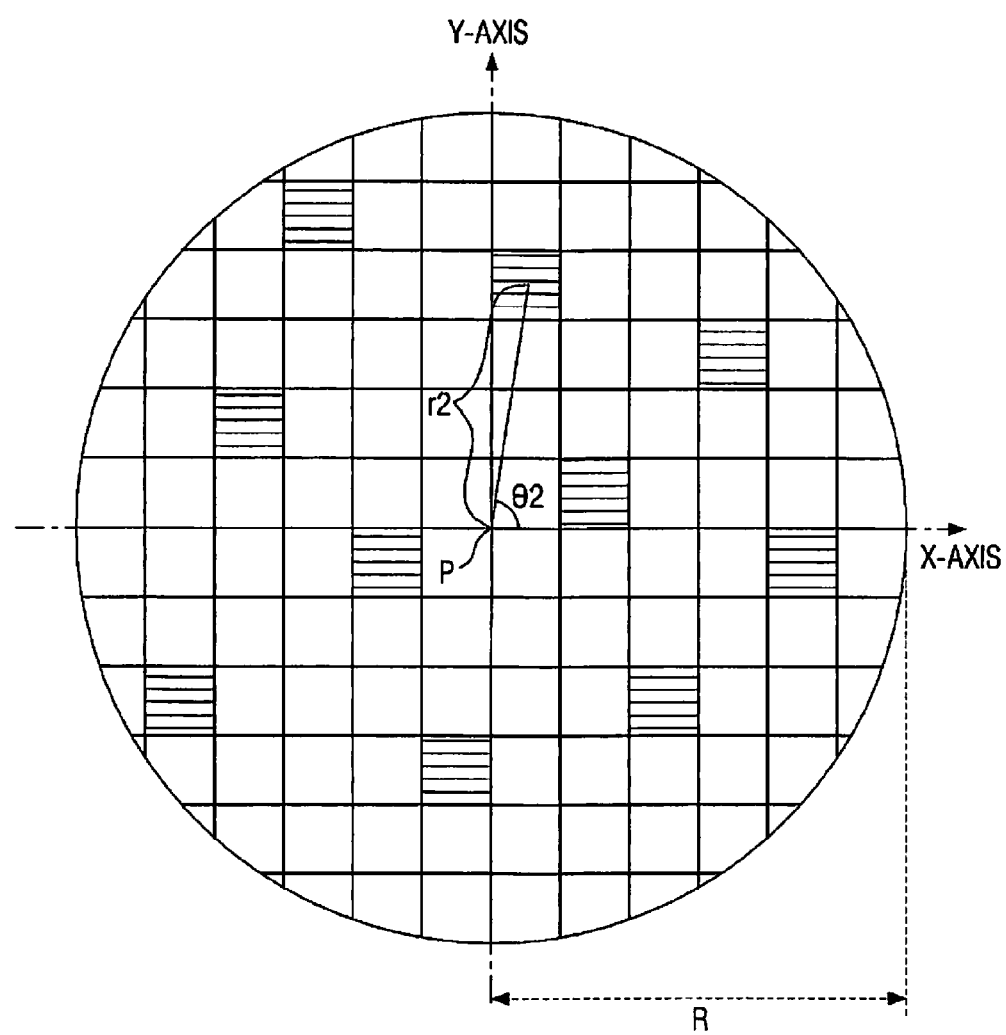
Figure 4:
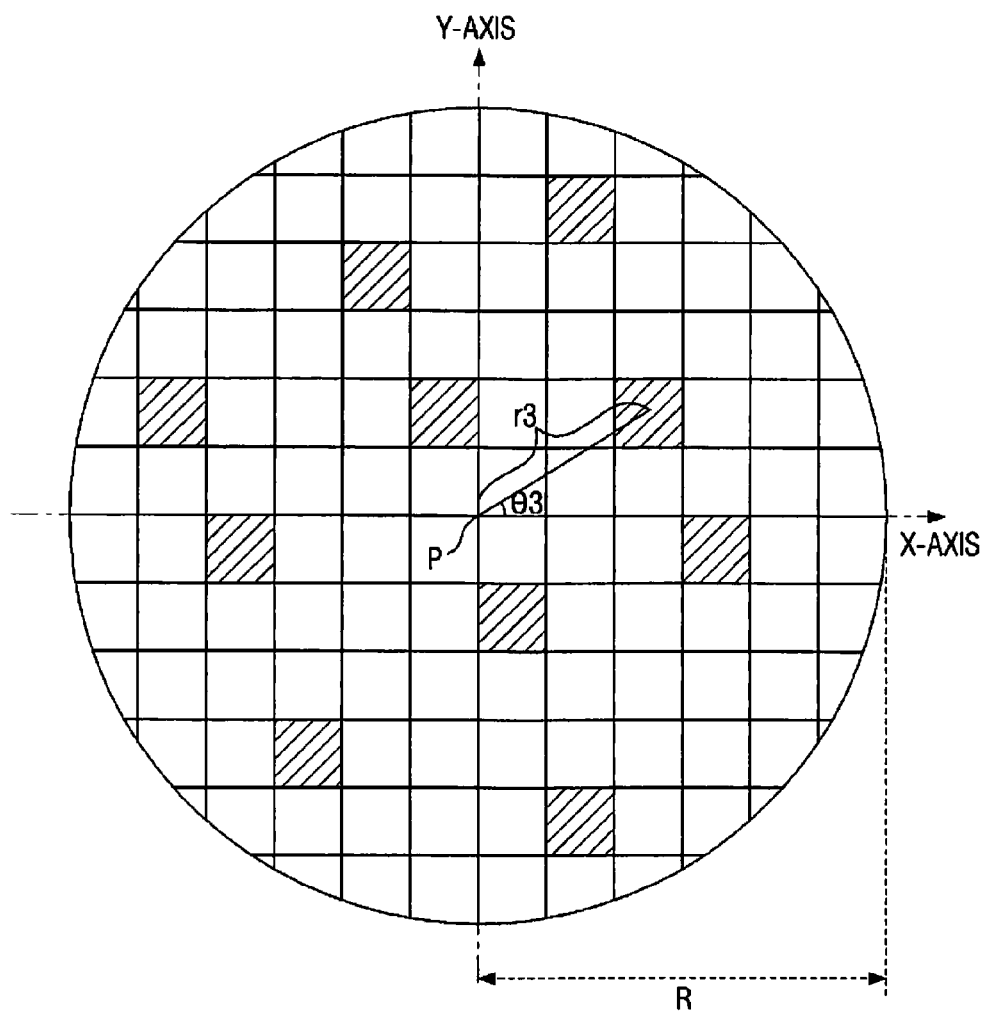
Figure 5:
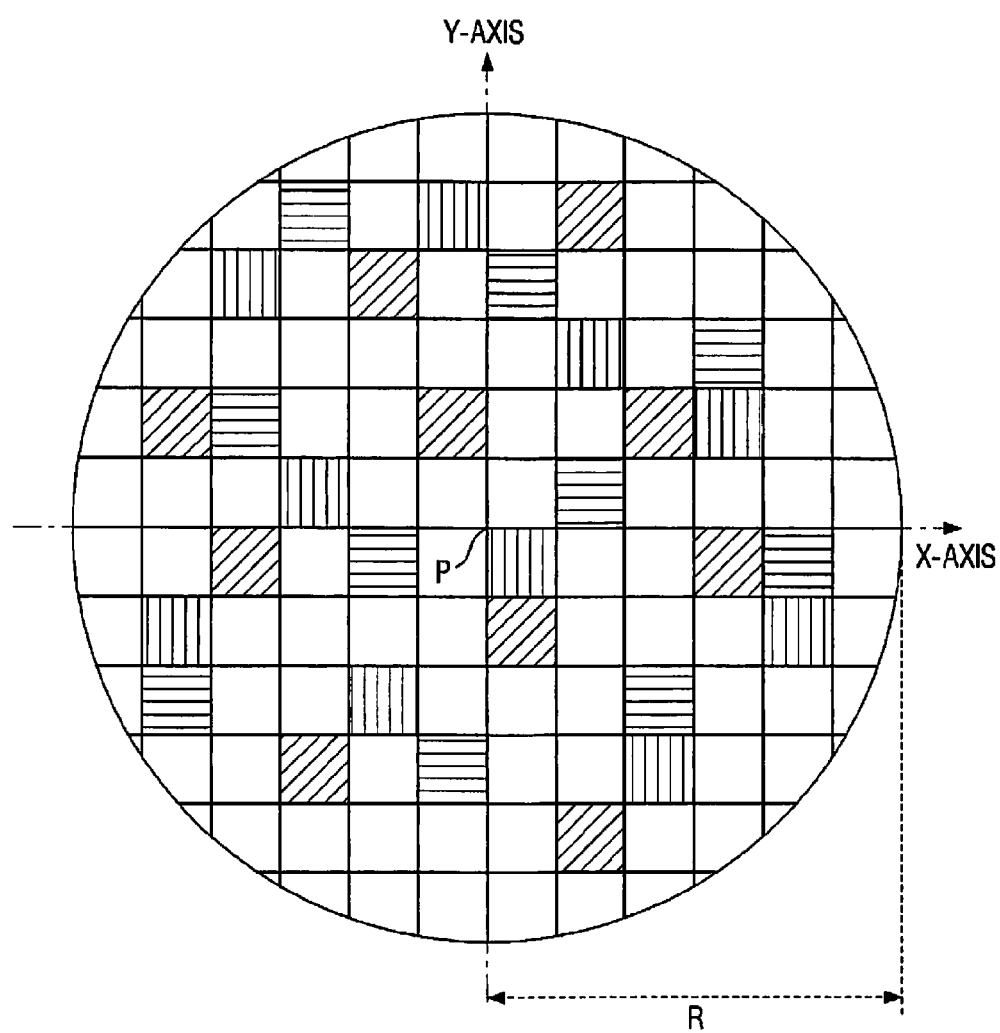
FIG. 5 is a diagram illustrating a combination of the polar coordinate sets of FIG. 2 to FIG. 4.

FIG. 1 is a diagram illustrating a wafer inspection apparatus according to an example embodiment of the present inventive concepts. FIG. 2 to FIG. 4 are diagrams illustrating polar coordinate sets derived by the wafer inspection apparatus according to an example embodiment of the present inventive concepts. FIG. 5 is a diagram illustrating a combination of the polar coordinate sets of FIG. 2 to FIG. 4.

Referring to FIG. 1, a wafer inspection apparatus 100 includes a support 110, a derivation unit 120, an inspection unit 130 and a calculation unit 140.

The support 110 may supply a wafer W to the wafer inspection apparatus 100. Further, the support 110 may support the wafer W that is supplied to the wafer inspection apparatus 100.

A plurality of wafers W1, W2 and W3 may be disposed on the support 110. The support 110 may sequentially locate the wafer W disposed on the support 110 under the inspection unit 130. In the present disclosure, a plurality of wafers W1, W2, and W3 may be interchangeably and collectively referred to as the water W. The water W may also refer to an imaginary wafer (e.g., a virtual single wafer), on which defect inspection results of the respective wafers W1, W2, and W3 based on the first to third polar coordinate sets are combined.

For example, the support 110 may locate the first wafer W1 under the inspection unit 130. The support 110 may locate the second wafer W2 under the inspection unit 130, after the defect inspection of the first wafer W1 is performed. Moreover, the support 110 may locate the third wafer W3 under the inspection unit 130, after the defect inspection of the second wafer W2 is performed. Consequently, the wafer inspection apparatus 100 may perform the defect inspection of a plurality of wafers W1, W2 and W3, for example, by moving the support 110.

The wafer W, for example, may be a substrate formed of bulk silicon. According to some example embodiments, the wafer W may also be a silicon substrate or may contain other materials, for example, silicon germanium, indium antimonide, lead telluride, indium arsenide, indium phosphide, gallium arsenide or gallium antimonide. The wafer W may have a configuration in which an epitaxial layer is disposed on a base substrate.

Further, the wafer W, for example, may include a semiconductor device having a three-dimensional structure.

In FIG. 1, although three wafers W1, W2 and W3 are illustrated as being disposed on the support 110, four or more wafers may be disposed on the support 110.

The derivation unit 120 may derive a plurality of polar coordinate sets, using a latin hypercube sampling. For example, the derivation unit 120 may derive a plurality of polar coordinate sets in which the respective coordinates do not overlap one another, using the latin hypercube sampling.

Referring to FIG. 2 to FIG. 5, the plurality of polar coordinate sets 160 may include a first polar coordinate set 161, a second polar coordinate set 162 that does not overlap the first polar coordinate set 161, and a first third polar coordinate set 163 that does not overlap the first and second polar coordinate sets 161 and 162.

However, example embodiments of the present inventive concepts are not limited thereto. That is, in some example embodiments, a plurality of polar coordinate sets 160 may include four or more polar coordinate sets that do not overlap one another. In some other example embodiments, a plurality of polar coordinate sets 160 may include two polar coordinate sets that do not overlap each other.

The first to third polar coordinate sets 161, 162 and 163 may be formed on the polar coordinates that are made up of distances r1, r2 and r3 and angles θ1, θ2 and θ3. The distances r1, r2 and r3 are distances from an origin P of the wafer W to the respective polar coordinates, and the angles θ1, θ2 and θ3 are angles formed between a line connecting the origin P of the wafer W with the respective polar coordinates and an X-axis.

In FIG. 1, although the derivation unit 120 is illustrated as being disposed on the inspection unit 130, the position of the derivation unit 120 is not limited thereto.

The inspection unit 130 may be disposed on the support 110 to perform the defect inspection of the wafer W. For example, the inspection unit 130 may irradiate the wafer W with at least one of beam, ultraviolet ray, or electron. The inspection unit 130 may perform the defect inspection of the wafer W by a visual observation of an operator.

The inspection unit 130 may receive signals of a plurality of polar coordinate sets 160 derived from the derivation unit 120. The inspection unit 130 may perform a defect inspection of the wafer W, using the plurality of polar coordinate sets 160 received from the derivation unit 120.

For example, the inspection unit 130 may perform the defect inspection of the first wafer W1 using the first polar coordinate set 161, may perform the defect inspection of the second wafer W2 using the second polar coordinate set 162, and may perform the defect inspection of the third wafer W3 using the third polar coordinate set 163.

However, example embodiments of the present inventive concepts are not limited thereto. That is, in some example embodiments, the defect inspection of the first wafer W1 may be performed using the first polar coordinate set 161 and the third polar coordinate set 163. Further, the defect inspection of the second wafer W2 may be performed using the second polar coordinate set 162 and a fourth polar coordinate set (not shown), which does not overlap the first to third polar coordinate sets 161, 162 and 163.

In some other example embodiments, the defect inspection of the first wafer W1 and the third wafer W3 may be performed using the first polar coordinate set 161. Further, the defect inspection of the second wafer W2 and the fourth wafer (not shown), which is different from the first through third wafers W1, W2 and W3, may be performed using the second polar coordinate set 162.

The inspection unit 130 may transmit the defect inspections result of the respective wafers W1, W2 and W3 to the calculation unit.

The calculation unit 140 may receive the defect inspection result of the respective wafers W1, W2 and W3 transmitted from the inspection unit 130 and may combine the defect inspection results of the wafer W.

For example, the calculation unit 140 may receive the defect inspection result of the first wafer W1 using the first polar coordinate set 161 from the inspection unit 130, the defect inspection result of the second wafer W2 using the second polar coordinate set 162, and the defect inspection result of the third wafer W3 using the third polar coordinate set 163. The calculation unit 140 may combine the defect inspection results of the first to third wafer W1, W2 and W3 received from the inspection unit 130.

As illustrated in FIG. 5, the first to third polar coordinate sets 161, 162 and 163 may be relatively evenly distributed over the entire region of the wafer W, without overlapping one another. Thus, by combining the defect inspection results of the respective wafers W1, W2 and W3 using the first to third polar coordinate sets 161, 162 and 163, the defect inspection over the entire region on the wafer W (e.g., a single wafer) may be performed.

Hereinafter, a combination of polar coordinate sets derived by an wafer inspection apparatus according to another example embodiment of the present inventive concepts will be described referring to FIG. 6.

Figure 6:
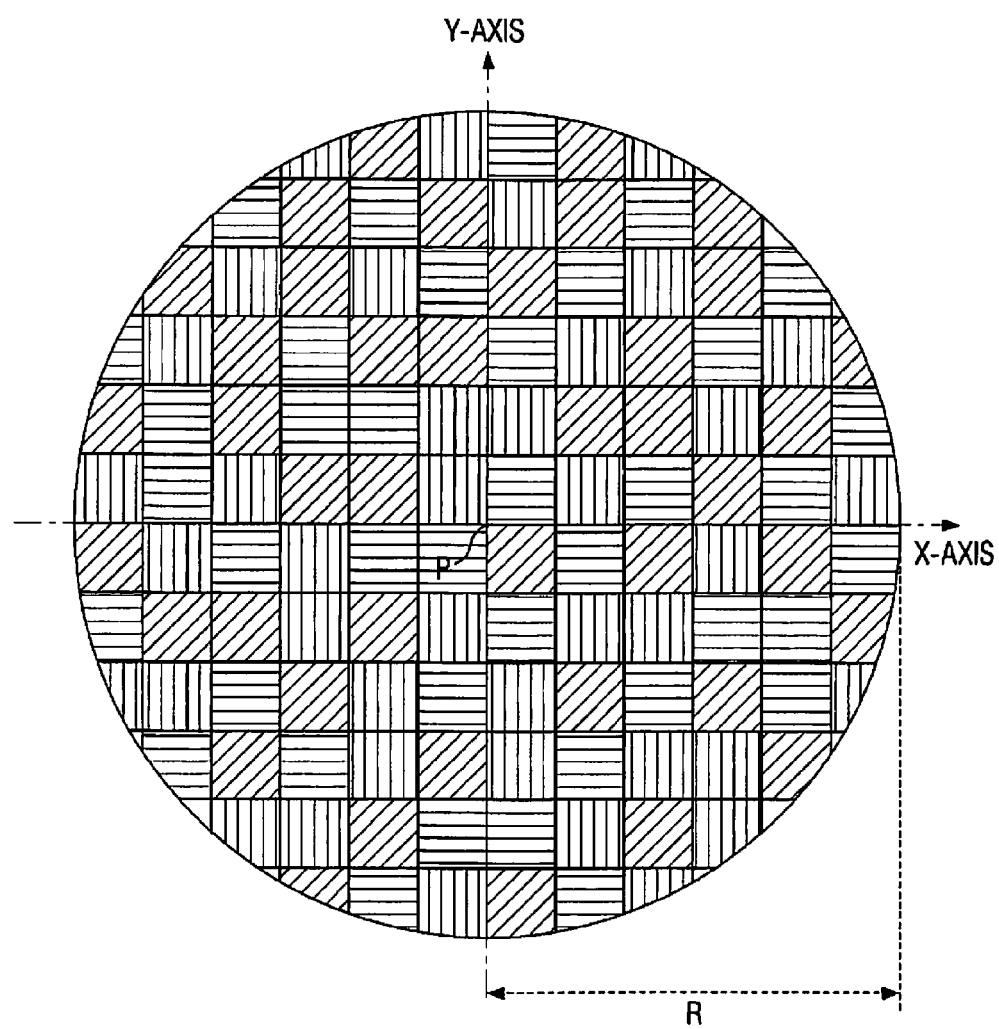
FIG. 6 is a diagram illustrating a combination of polar coordinate sets derived by the wafer inspection apparatus according to another example embodiment of the present inventive concepts.

FIG. 6 is a diagram illustrating a combination of polar coordinate sets derived by a wafer inspection apparatus according to another example embodiment of the present inventive concepts.

Unlike the plurality of polar coordinate sets 160 of FIG. 5, a plurality of polar coordinate sets 260 may substantially completely fill the surface of the wafer W. For example, as illustrated in FIG. 6, the surface of the wafer W may be completely filled by the combination of the respective polar coordinates sets. Thus, a defect inspection of the entire region of the wafer W may be performed by the combination of polar coordinate sets.

Hereinafter, a wafer inspection method of a wafer inspection apparatus according to an example embodiment of the present inventive concepts will be described referring to FIG. 7 to FIG. 10.

Figure 7:
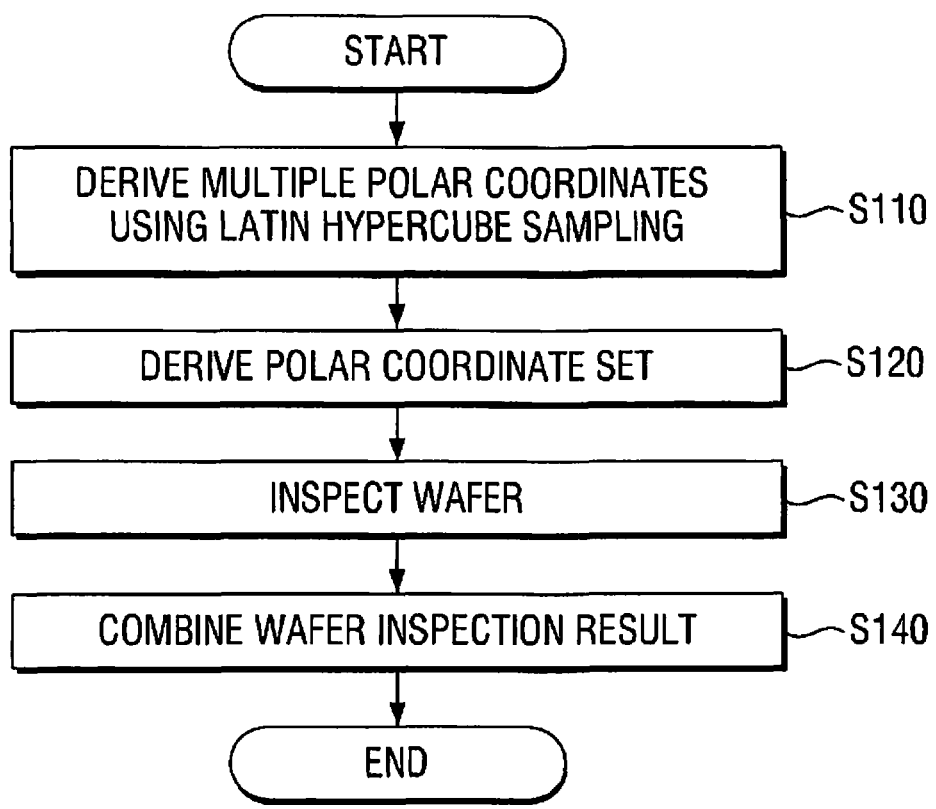
FIG. 7 is a flow chart sequentially illustrating a wafer inspection method of the wafer inspection apparatus according to an example embodiment of the present inventive concepts.
Figure 8:
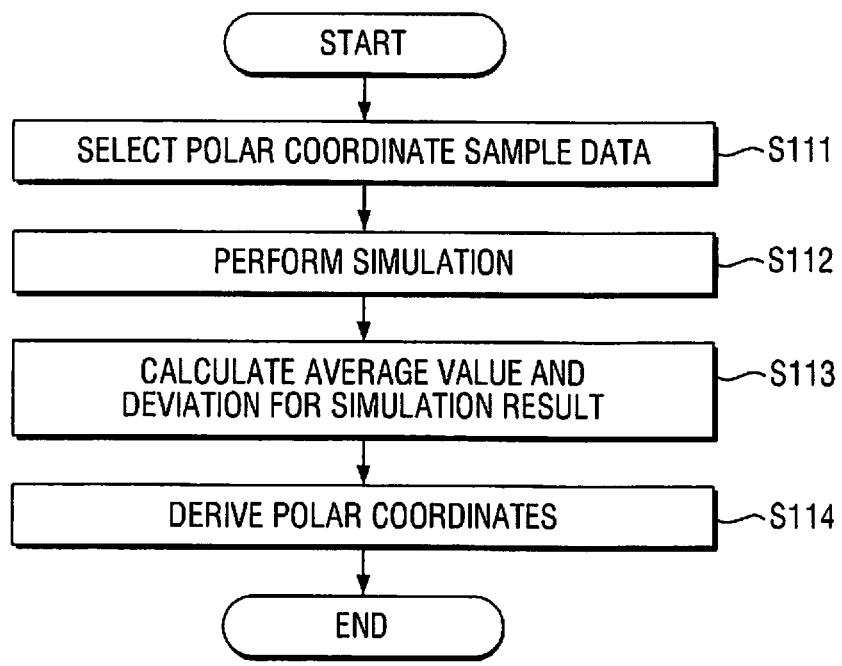
FIG. 8 is a flow chart sequentially illustrating a method of deriving a plurality of polar coordinates by a latin hypercube sampling method according to an example embodiment of the present inventive concepts.
Figure 9:
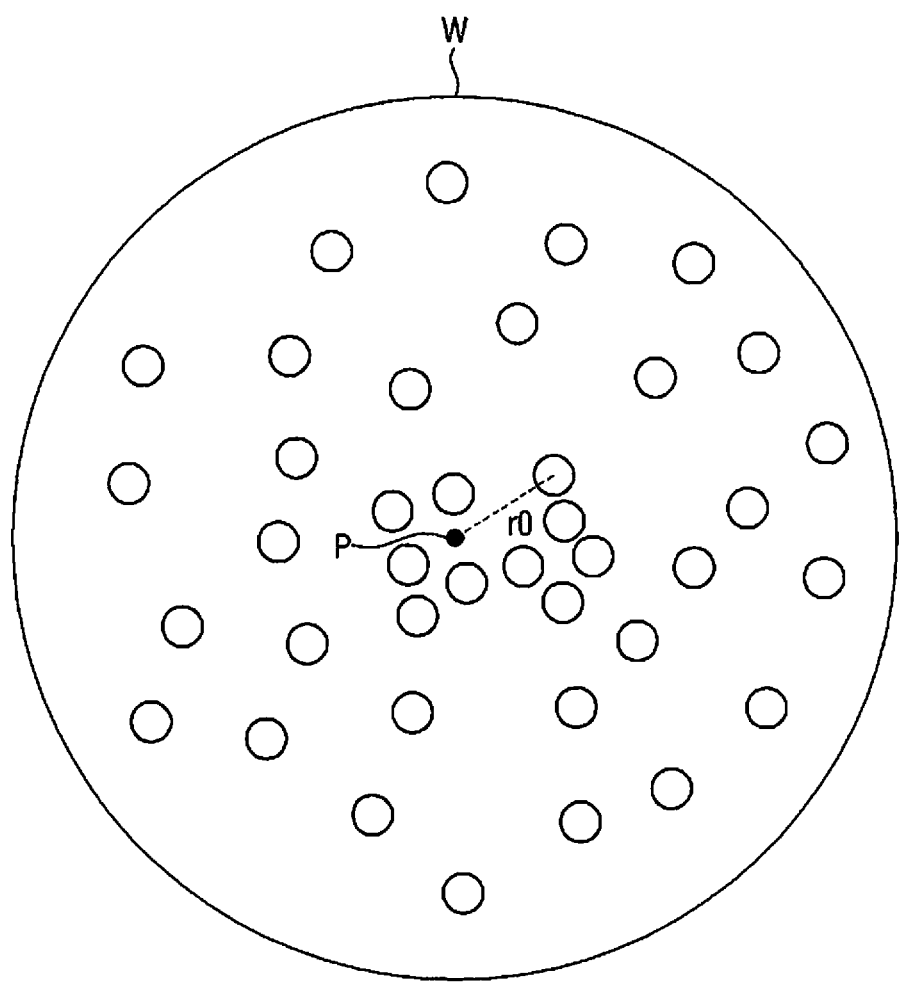
FIG. 9 is a diagram illustrating a plurality of polar coordinates derived by the latin hypercube sampling method according to an example embodiment of the present inventive concepts.
Figure 10:
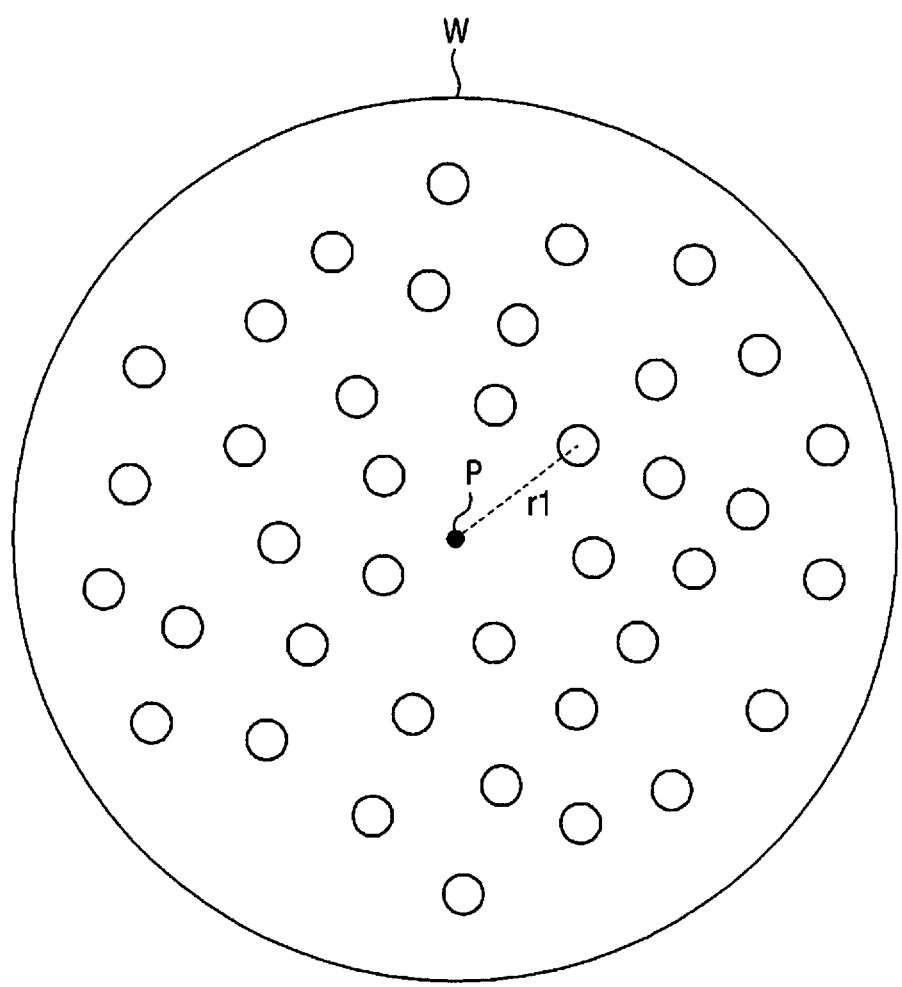
FIG. 10 is a diagram illustrating derivation of polar coordinate sets performed by replacing some of polar coordinate sets derived by the latin hypercube sampling method according to an example embodiments of the present inventive concepts.

FIG. 7 is a flow chart sequentially illustrating a wafer inspection method of the wafer inspection apparatus according to an example embodiment of the present inventive concepts. FIG. 8 is a flow chart sequentially illustrating a method of deriving a plurality of polar coordinates by a latin hypercube sampling method according to an example embodiment of the present inventive concepts. FIG. 9 is a diagram illustrating a plurality of polar coordinates derived by the latin hypercube sampling method according to an example embodiment of the present inventive concepts. FIG. 10 is a diagram illustrating derivation of polar coordinate sets by replacing some of polar coordinate sets derived by the latin hypercube sampling method according to an example embodiment of the present inventive concepts.

Referring to FIG. 7 and FIG. 9, the derivation unit 120 may derive a plurality of polar coordinates, using the latin hypercube sampling (S110).

For example, referring to FIG. 8, the derivation unit 120 may set (1) the distance from the origin P of the wafer W to the respective polar coordinates and (2) an angle formed between the line connecting the origin P of the wafer W with the respective polar coordinates and the X-axis on the polar coordinates on the wafer W as variables using the latin hypercube sampling. The derivation unit 120 may select the sample data of the plurality of polar coordinates (e.g., a number of polar coordinates), in consideration of the space and variables of the wafer W (S111).

The derivation unit 120 may perform a simulation using the sample data of the plurality of selected polar coordinates so that the polar coordinates do not overlap one another (S112).

Next, the derivation unit 120 may calculate the average values and deviations of the result values of the plurality of polar coordinates derived through the simulation (S113).

The derivation unit 120 may derive a plurality of select polar coordinates 150 such that the select polar coordinates are distributed over the entire region on the wafer W, using the average values and deviations of the result values of the plurality of polar coordinates (S114).

Referring to FIG. 7, FIG. 9 and FIG. 10, some coordinates of the plurality of polar coordinates 150 derived using the latin hypercube sampling may be distributed to be concentrated around the origin P of the wafer W, as illustrated in FIG. 9.

The derivation unit 120 may replace a distance r0 from each of the plurality of polar coordinates 150 to the origin of the wafer W with a square root of a value obtained by multiplying the distance r0 from the each of the plurality of polar coordinates 150 to the origin of the water W by a radius R of the wafer W.

Thus, the some coordinates of the plurality of polar coordinates 150 having the concentrated distribution around the origin P of the wafer W may be relatively evenly distributed over the entire region of the wafer W.

Accordingly, as illustrated in FIG. 10, the derivation unit 120 may derive the first polar coordinate set 151 having the respective polar coordinates relatively evenly distributed over the entire region on the wafer W, using the substituted value r1 (S120). The above description may be represented by the following formula.

$$r1 = \sqrt{R * r0}$$

The derivation unit 120 may derive a plurality of polar coordinate sets 161, 162 and 163d that does not overlap one another, by repeating such a process.

The inspection unit 130 may perform the defect inspection of the first wafer W1 using the first polar coordinate set 161, may perform the defect inspection of the second wafer W2 using the second polar coordinate set 162, and may perform the defect inspection of the third wafer W3 using the third polar coordinate set 163 (S130).

The calculating unit 140 may perform the defect inspection of the wafer W by combining the defect inspection results of the first to third wafer W1, W2 and W3 (S140).

The wafer inspection apparatus 100 of the present inventive concepts may reduce the defect inspection time for the wafer W by combining a plurality of polar coordinate sets that does not overlap each other, and may inspect the defects relatively evenly over the entire region on the wafer W.

Hereinafter, a wafer inspection method of the wafer inspection apparatus according to still another example embodiment of the present inventive concepts will be described referring to FIG. 11 to FIG. 15. Differences from the wafer inspection apparatus illustrated in FIG. 7 will be mainly described.

Figure 11:
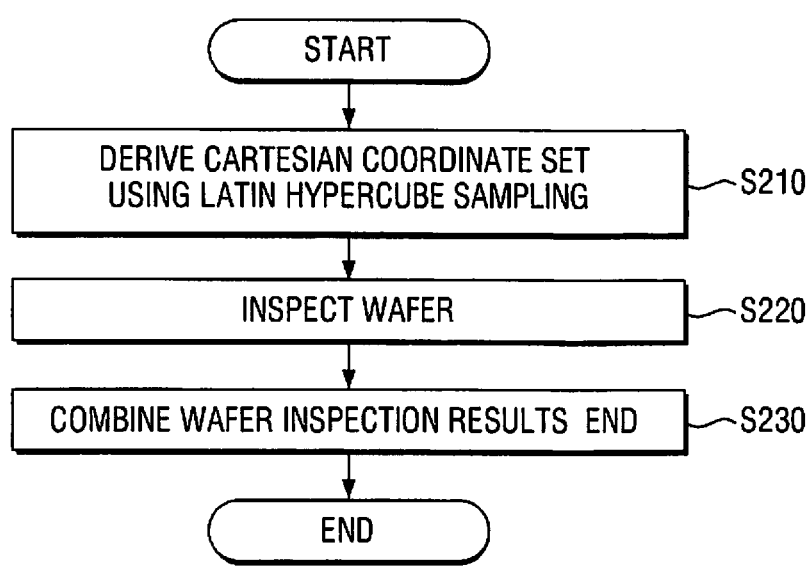
FIG. 11 is a flow chart sequentially illustrating a wafer inspection method of the water inspection apparatus according to an example embodiment of the present inventive concepts.
Figure 12:
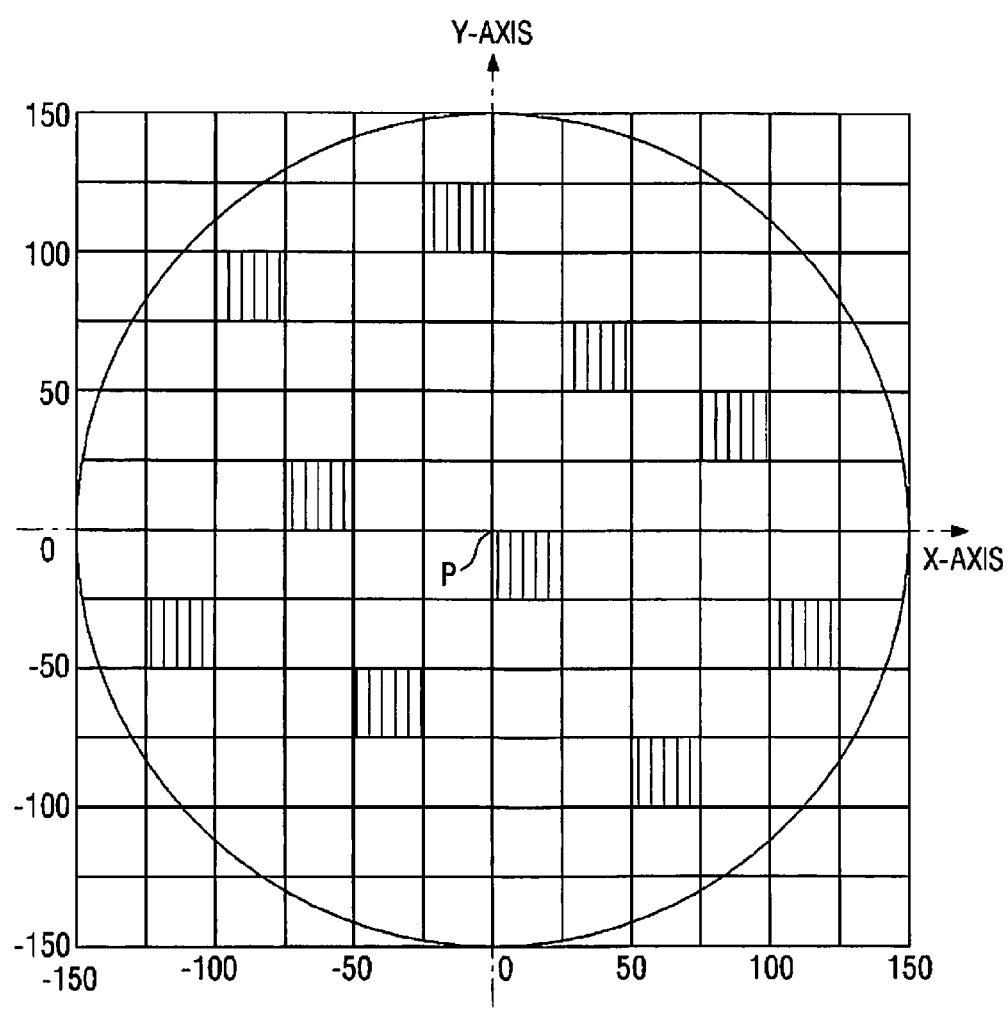
FIG. 12 to FIG. 14 are diagrams illustrating cartesian coordinate sets derived by the wafer inspection apparatus according to an example embodiment of the present inventive concepts.
Figure 13:
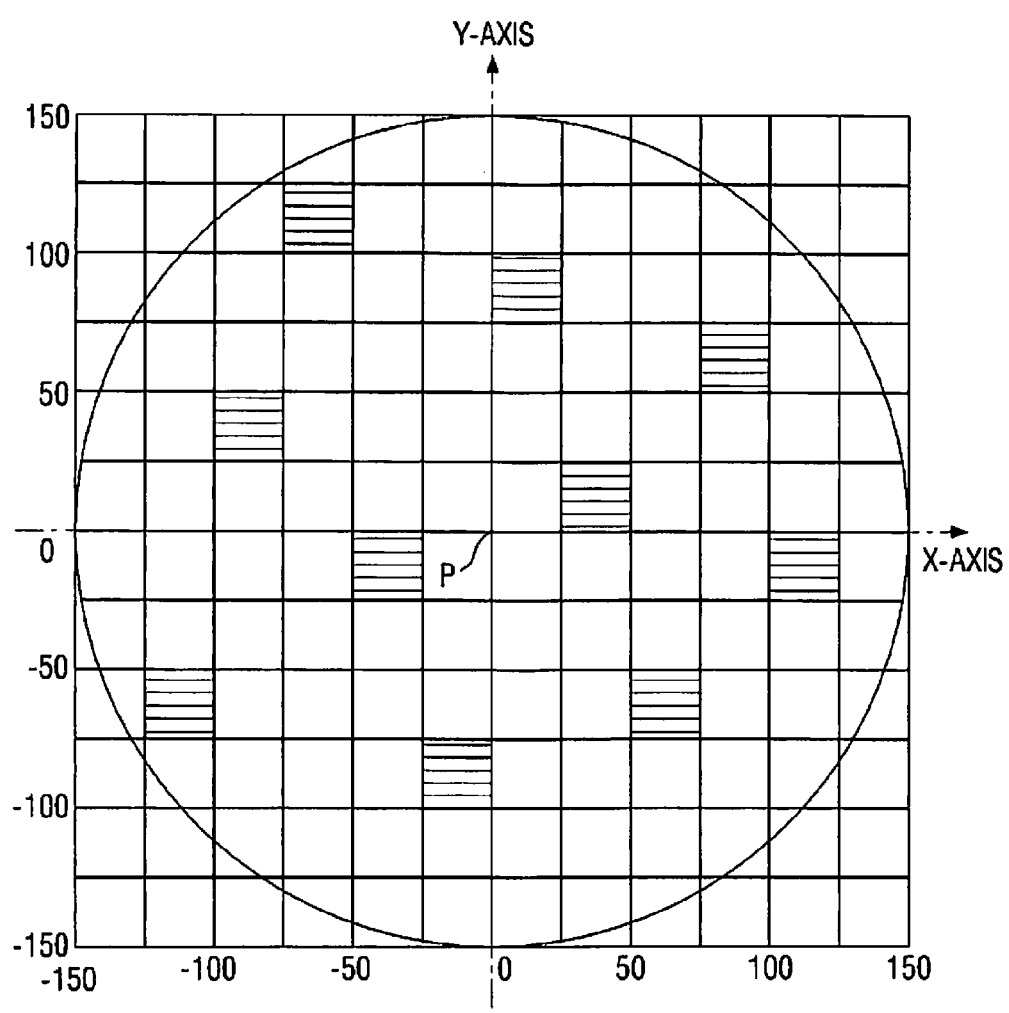
Figure 14:
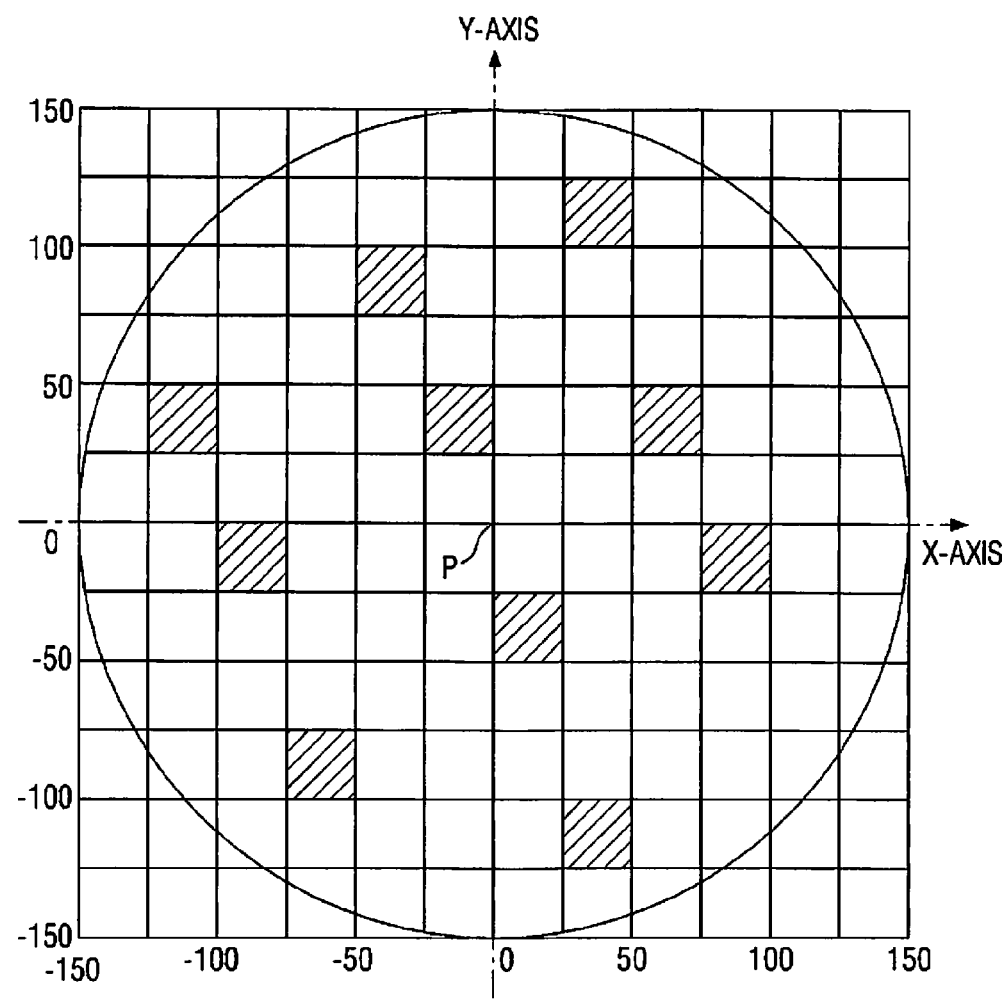
Figure 15:
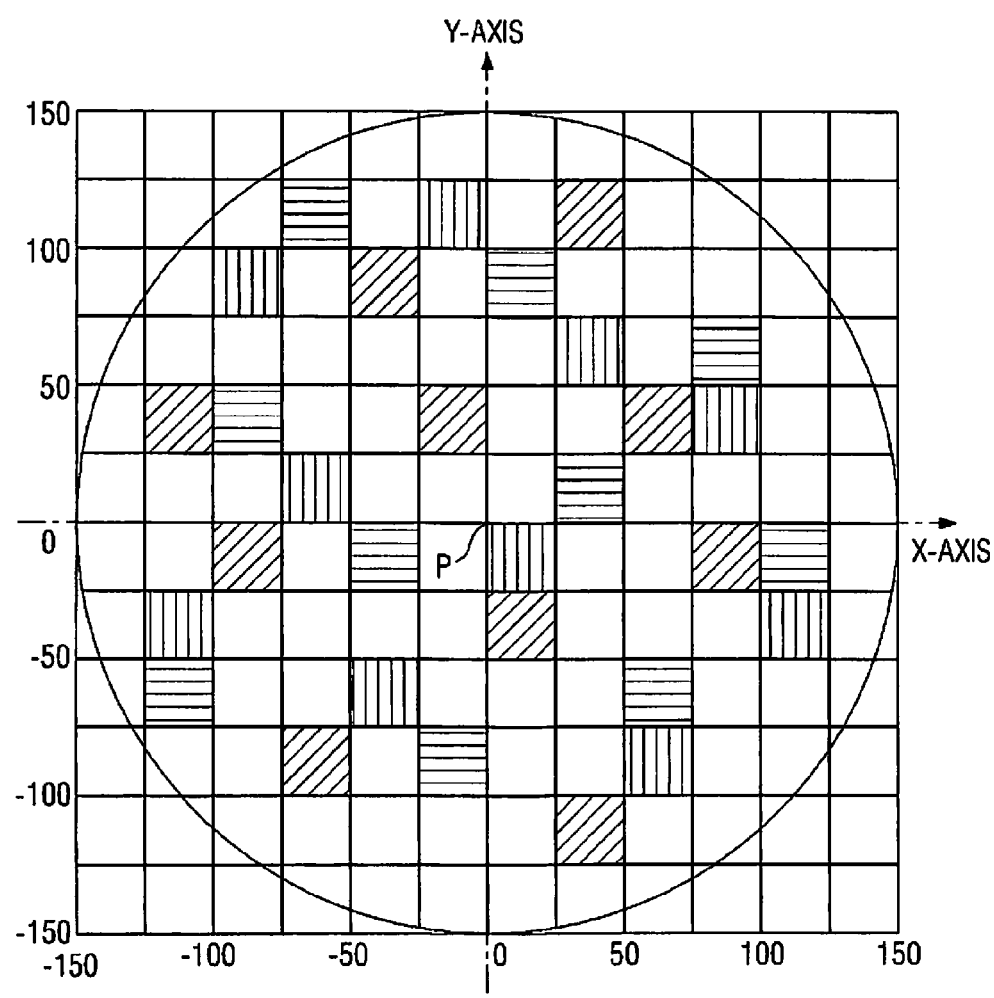
FIG. 15 is a diagram illustrating a combination of the cartesian coordinate sets of FIG. 12 to FIG. 14.

FIG. 11 is a flow chart sequentially illustrating a wafer inspection method of the wafer inspection apparatus according to an example embodiment of the present inventive concepts. FIG. 12 to FIG. 14 are diagrams illustrating cartesian coordinate sets derived by the wafer inspection apparatus according to an example embodiment of the present inventive concepts. FIG. 15 is a diagram illustrating a combination of the cartesian coordinate sets of FIG. 12 to FIG. 14.

Referring to FIG. 11, the wafer inspection apparatus 100 may be configured so that a derivation unit 120 derives a plurality of cartesian coordinate sets using the latin hypercube sampling (S210).

For example, the derivation unit 120 may set (1) positions on the X-axis of the respective cartesian coordinates and (2) positions on the Y-axis of the respective cartesian coordinates on the cartesian coordinate system of the wafer W as variables, using the latin hypercube sampling. The derivation unit 120 may select the sample data of a plurality of cartesian coordinates (e.g., a number of cartesian coordinates), in consideration of the space and variables of the wafer W.

The derivation unit 120 may perform a simulation using the sample data of the plurality of selected cartesian coordinates so that the respective cartesian coordinates do not overlap one another.

Next, the derivation unit 120 may calculate the average values and deviations of the result values of the plurality of cartesian coordinates derived through the simulation.

The derivation unit 120 may derive a plurality of select cartesian coordinate sets 270 in which the respective cartesian coordinates are distributed over the entire region on the wafer W, using the average value and deviation of the result values of the plurality of cartesian coordinates.

Referring to FIG. 12 to FIG. 15, a plurality of cartesian coordinate sets 270 may include a first cartesian coordinate net 271, a second cartesian coordinate set 272 that does not overlap the first cartesian coordinate set 271, and a third cartesian coordinate set 273 that does not overlap the first and second cartesian coordinate sets 271 and 272.

However, example embodiments of the present inventive concepts are not limited thereto. That is, in some example embodiments, a plurality of cartesian coordinate sets 270 may include four or more cartesian coordinate sets that do not overlap one another. Also, in some other example embodiments, the plurality of cartesian coordinate sets 270 may include two cartesian coordinate sets that do not overlap each other.

The first to third cartesian coordinate sets 271, 272, and 273 may be formed on the cartesian coordinate system including the X-axis and the Y-axis.

Referring to FIG. 11, the inspection unit 130 may perform the defect inspection of the first wafer W1 using the first cartesian coordinate set 271, may perform the defect inspection of the second wafer W2 using the second cartesian coordinate set 272, and may perform the defect inspection of the third wafer W3 using the third cartesian coordinate set 273 (S220).

However, example embodiments of the present inventive concepts are not limited thereto. That is, in some example embodiments, the defect inspection of the first wafer W1 may be performed using the first cartesian coordinate set 271 and the third cartesian coordinate set 273. Further, the detect inspection of the second wafer W2 may be performed, using the second cartesian coordinate set 272, and the fourth cartesian coordinate (not shown) set that does not overlap the first to third cartesian coordinate sets 271, 272 and 273.

Also, in some other example embodiments, the defect inspection of the first wafer W1 and the third wafer W3 may be performed using the first cartesian coordinate set 271. Also, the defect inspection of the second wafer W2 and the fourth wafer (now shown), which is different from the first to third wafers W1, W2 and W3, may be performed using the second cartesian coordinate set 272.

The inspection unit 130 may transmit the defect inspection results of respective wafers W1, W2 and W3 to the calculation unit 140.

The calculation unit 140 may receive the defect inspection results of the respective wafers W1, W2 and W3 transmitted from the inspection unit 130 and may combine the defect inspection results of the wafer W (S230).

Hereinafter, a wafer inspection method of the wafer inspection apparatus according to still another embodiment of the present inventive concepts will be described referring to FIG. 16. Differences from the wafer inspection apparatus of FIG. 11 will be mainly described.

Figure 16:
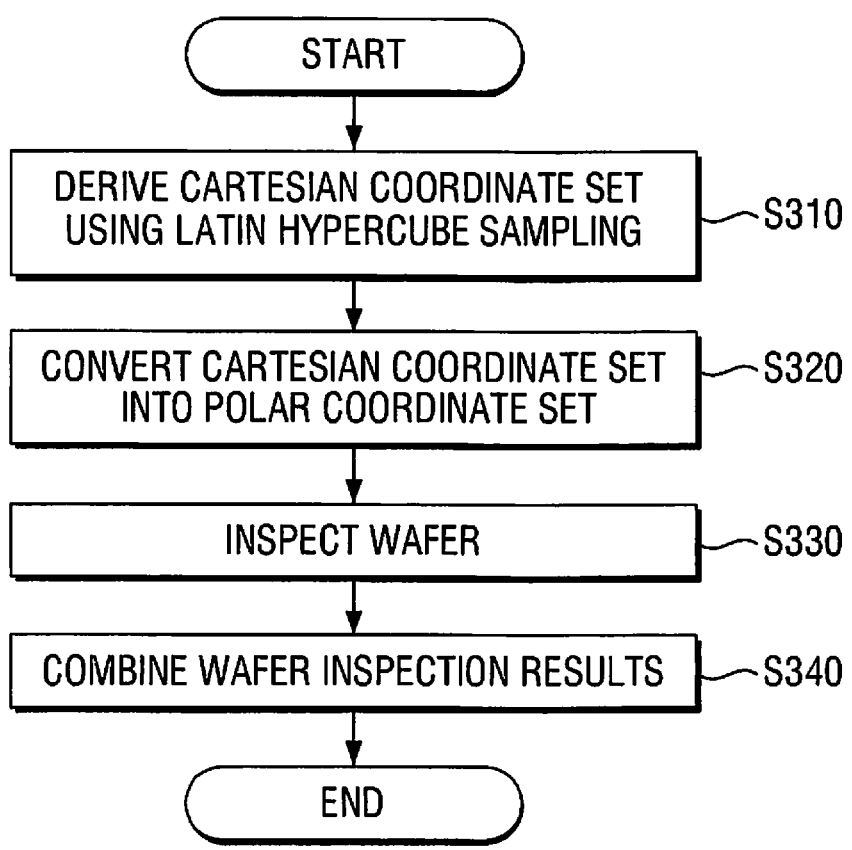
FIG. 16 is a flow chart sequentially illustrating a wafer inspection method of the wafer inspection apparatus according to an example embodiment of the present inventive concepts.

FIG. 16 is a flow chart sequentially illustrating a wafer inspection method of the wafer inspection apparatus according to an example embodiment of the present inventive concepts.

Referring to FIG. 16, the derivation unit 120 of the wafer inspection apparatus 100 may derive a plurality of cartesian coordinate sets 271, 272, and 273 (as shown in FIGS. 12-14) using the latin hypercube sampling (S310), and the calculation unit 140 may convert the respective cartesian coordinate sets 271, 272 and 273 derived from the derivation unit 120 into the respective polar coordinate sets 161, 162 and 163 (as shown in FIGS. 2-4) (S320).

For example, the calculation unit 140 may receive a plurality of cartesian coordinate sets 270 derived from the derivation unit 120. The calculation unit 140 may convert the first cartesian coordinate set 271 into the first polar coordinate set 161, may convert the second cartesian coordinate set 272 into the second polar coordinate set 162, and may convert the third cartesian coordinate set 273 into the third polar coordinate set 163.

Next, the inspection unit 130 may receive the first to third polar coordinate sets 161, 162 and 163 from the calculation unit 140. The inspection unit 130 may perform the defect inspection of the first wafer W1 using the first polar coordinate set 161, may perform the defect inspection of the second wafer W2 using the second polar coordinate set 162, and may perform the defect inspection of the third wafer W3 using the third polar coordinate set 163 (S330).

The calculation unit may receive the defect inspection results of the respective wafers W1, W2, and W3 transmitted from the inspection unit 130 and may combine the defect inspection results of the wafer W (S340).

The units (e.g., derivation unit 120 and the calculation unit 140) described herein may be implemented using hardware components and/or a combination of hardware and software components. For example, the hardware components may include processing devices. A processing device may be implemented using one or more hardware devices configured to carry out and/or execute program code by performing arithmetical, logical, and input/output operations. The processing device(s) may include a processor, a controller and an arithmetic logic unit, a digital signal processor, a microcomputer, a field programmable array, a programmable logic unit, a microprocessor or any other device capable of responding to and executing instructions in a defined manner. The processing device(s) may also include storage devices such as a memory. The processing device may run an operating system (OS) and/or one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and/or multiple types of processing elements. For example, a processing device may include multiple processors or a processor and a controller. Further, different processing configurations are possible, such a parallel processors.

The software may include a computer program, a piece of code, an instruction, or some combination thereof, to independently or collectively instruct and/or configure the processing device to operate as desired, thereby transforming the processing device into a special purpose processor. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

Hereinafter, an electronic system including the semiconductor device formed by using the wafer inspection apparatus according to some example embodiments of the present inventive concepts will be described with reference to FIG. 17.

Figure 17:
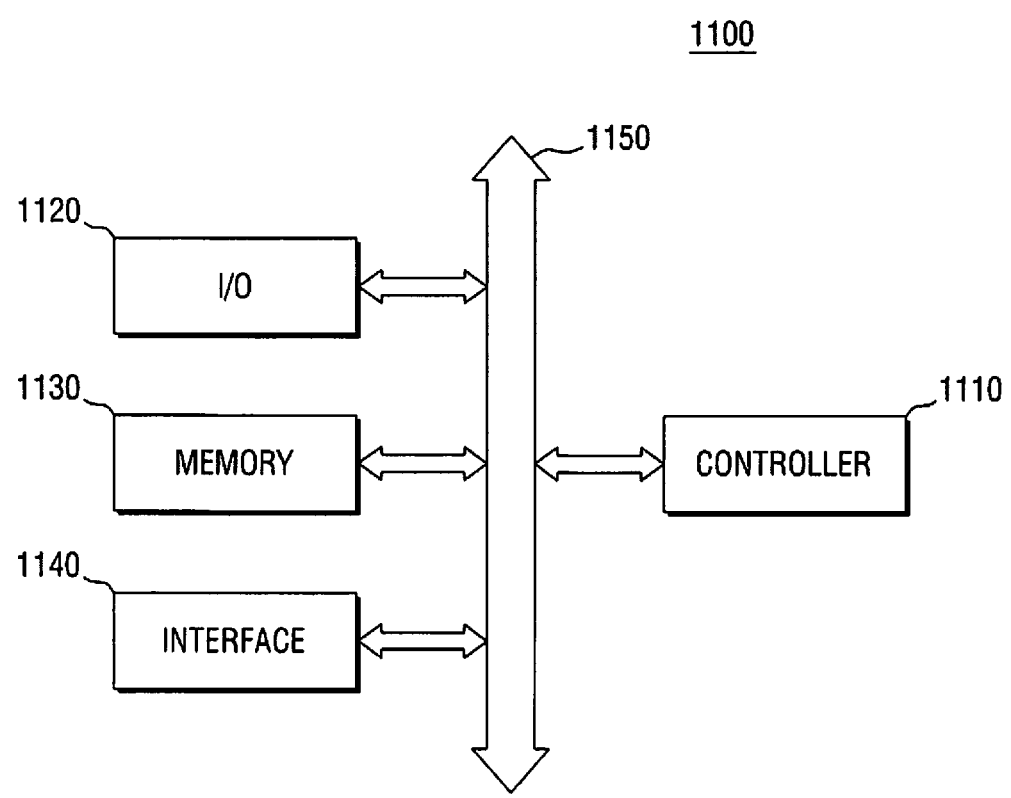
FIG. 17 is a block diagram of an electronic system including a semiconductor device formed, using the wafer inspection apparatus according to an example embodiments of the present inventive concepts.

FIG. 17 is a block diagram of an electronic system including the semiconductor device formed using the wafer inspection apparatus according to an example embodiments of the present inventive concepts.

Referring to FIG. 17, the electronic system 1100 according to an example embodiment of the present inventive concepts may include a controller 1110, an input/output (110) device 1120, a memory device 1130, an interface 1140 and a bus 1150.

The controller 1110, the I/O device 1120, the memory device 1130 and/or the interface 1140 may be connected to one another through the bus 1150. The bus 1150 corresponds to a path through which the data are moved.

The controller 1110 may include at least one of a microprocessor, a digital signal processor, a microcontroller and logic devices capable of performing similar functions to the elements.

The I/O device 1120 may include, for example, a keypad, a keyboard, and/or a display device. The memory device 1130 may store data and/or commands.

The interface 1140 may serve to transmit data to or receive data from a communication network. The interface 1140 may be a wired or wireless interface. For example, the interface 1140 may include an antenna or a wired or wireless transceiver. Furthermore, the electronic system 1100 may be an operating memory for improving the operation of the controller 1110, and may also include a high-speed DRAM or SRAM.

Further, the semiconductor device manufactured according to the example embodiment of the present inventive concepts may be provided in the memory device 1130 or may be provided as a part of the controller 1110, the I/O device 1120 or the like.

The electronic system 1100 may be applied to various types of electronic products, which are capable of transmitting or receiving information in a wireless environment, such as a personal digital assistant (PDA), a portable computer, a web tablet, a wireless phone, a mobile phone, a digital music player and a memory card.

While the present inventive concepts has been particularly illustrated and described with reference to some example embodiments thereof, it will be understood by those of ordinary skill in the art that various changes in form and detail may be made therein without departing from the spirit and scope of the present inventive concepts as defined by the following claims. The example embodiments should be considered in a descriptive sense only and not for purposes of limitation.

What is claimed is:

1. A wafer inspection apparatus comprising:
   a support unit configured to support a first wafer and a second wafer;
   a memory having computer-readable instructions stored therein; and
   at least one processor configured to execute the computer-readable instructions to cause the wafer inspection apparatus to,
      derive a first polar coordinate set and a second polar coordinate set using a latin hypercube sampling such that the first and second polar coordinate sets do not overlap with each other and the first and second polar coordinate sets are distributed over an entire surface of a virtual wafer,
      cause an inspection unit to perform a first defect inspection of the first wafer with respect to the first polar coordinate set and perform a second defect inspection of the second wafer with respect to the second polar coordinate set,
      receive a result of the first defect inspection and a result of the second defect inspection, and combine the result of the first defect inspection with the result of the second defect inspection, and
      cause to represent a result of the combination on the virtual wafer,
   wherein each of the first and second polar coordinate sets is provided on a polar coordinate system that is made up of (1) a distance from an origin of the virtual wafer to the respective polar coordinates, and (2) an angle formed between a line connecting the origin of the virtual wafer with the respective polar coordinates and an X-axis.

2. The wafer inspection apparatus of claim 1, wherein the at least one processor is further configured to cause the inspection unit is configured to perform,
   the first defect inspection of the first wafer using the first polar coordinate set and a third polar coordinate set, the third polar coordinate set not overlapping the first and second polar coordinate sets, and
   the second defect inspection of the second wafer using the second polar coordinate set and a fourth polar coordinate set, the fourth polar coordinate set not overlapping the first to third polar coordinates.

3. The wafer inspection apparatus of claim 1, wherein the at least one processor is further configured to,
   derive a plurality of polar coordinates using the latin hypercube sampling, and
   derive the first polar coordinate set, by replacing each distance from each of the polar coordinates to the origin of the virtual wafer with a square root of a value obtained by multiplying the distance from the each of the polar coordinates to the origin of the virtual wafer by a radius of the virtual wafer.

4. The wafer inspection apparatus of claim 1, wherein the at least one processor is further configured to,
   derive three or more polar coordinate sets using the latin hypercube sampling, the three or more polar coordinate sets not overlap one another on the virtual wafer, and
   inspect a plurality of wafers including the first and second wafers using the polar coordinate sets.

5. The wafer inspection apparatus of claim 4, wherein the at least one processor are further configured to derive the three or more polar coordinate sets such that the combination of the three or more polar coordinates sets are distributed over the entire surface of the virtual wafer.

6. The wafer inspection apparatus of claim 1, wherein the at least one processor is configured to,
set, using the latin hypercube sampling, the distance from the origin of the virtual wafer to the respective polar coordinates and an angle between the line connecting the origin of the virtual wafer with the respective polar coordinates and the X-axis on the polar coordinate system of the virtual wafer as variables, and
derive the first and second polar coordinate sets such that the first and second polar coordinates are distributed over the entire surface of the virtual wafer.

7. The wafer inspection apparatus of claim 6, wherein the at least one processor is further configured to
select sample data in consideration of a space and the variables on the virtual wafer,
perform, a simulation using selected sample data of selected polar coordinates of the plurality of polar coordinates so that the selected polar coordinates do not overlap each other, and
obtain a respective average value and a respective deviation of result values of the simulation to derive the first and second polar coordinate sets.

8. A wafer inspection apparatus comprising:
a support unit configured to support a first wafer and a second wafer;
a memory having computer-readable instructions stored therein; and
at least one processor configured to execute the computer-readable instructions to cause the wafer inspection apparatus to,
derive a first cartesian coordinate set and a second cartesian coordinate set using a latin hypercube sampling, the first and second cartesian coordinate sets not overlapping each other, the first and second cartesian coordinate sets distributed over an entire surface of a virtual wafer, the first and second cartesian coordinate sets being sets of coordinates provided on a cartesian coordinate system made up of an X-axis and a Y-axis,
cause an inspection unit to perform a defect inspection of a first wafer using the first cartesian coordinate set,
cause the inspection unit to perform a defect inspection of a second wafer, which is different from the first wafer, using the second cartesian coordinate set, and
combine a defect inspection result of the first wafer with a defect inspection result of the second wafer.

9. The wafer inspection apparatus of claim 8, wherein the at least one processor is further configured to
convert the first cartesian coordinate set into a first polar coordinate set,
convert the second cartesian coordinate set into a second polar coordinate set,
combine the defect inspection result of the first wafer using the first polar coordinate set with the defect inspection result of the second wafer using the second polar coordinate set, and
represent the first and second polar coordinate sets on a polar coordinate system, the polar coordinate system made up of a distance from an origin of the virtual wafer to the respective polar coordinates, and an angle formed between a line connecting the respective polar coordinates with the origin of the virtual wafer and an-X axis.

10. The wafer inspection apparatus of claim 8, wherein the at least one processor is further configured to,
perform the defect inspection of the first wafer and a third wafer using the first cartesian coordinate set, the third wafer being different from the first and second wafers, and
perform the defect inspection of the second wafer and a fourth wafer using the second cartesian coordinate set, the fourth wafer being different from the first to third wafers.

11. The wafer inspection apparatus of claim 8, wherein the at least one processor is further configured to,
sets, using the latin hypercube sampling, positions on the X-axis and positions on the Y-axis of the respective cartesian coordinates on the cartesian coordinate system of the virtual wafer as variables, and
derive the first and second cartesian coordinate sets such that the first and second cartesian coordinates are distributed over the entire surface of the virtual wafer.

12. The wafer inspection apparatus of claim 11, wherein the at least one processor is further configured to,
select sample data, in consideration of a space and the variables on the virtual wafer,
perform simulations using selected sample data of selected Cartesian coordinates of the plurality of Cartesian coordinates so that the selected cartesian coordinates do not overlap each other, and
obtain average values and deviations of result values of the simulations to derive the first and second cartesian coordinate sets.

13. A wafer inspection apparatus comprising:
a memory having computer-readable instructions stored therein; and
at least one processor configured to execute the computer-readable instructions to cause the wafer inspection apparatus to,
derive a plurality of select polar coordinate sets using a latin hypercube sampling, the select polar coordinate sets not overlapping one another, the select polar coordinate sets provided on a polar coordinate system and including (1) a distance from an origin of the wafer to the respective select polar coordinates, and (2) an angle formed between a line connecting the origin of the wafer with the respective select polar coordinates and an X-axis,
inspect wafers for defects using the select polar coordinate sets, and
combine and represent defect inspection results on a virtual wafer.

14. The wafer inspection apparatus of claim 13, wherein the at least one processor is further configured to execute the computer-readable instructions to select the polar coordinate sets to distribute substantially over an entire surface of the virtual wafer.

15. The wafer inspection apparatus of claim 13, wherein the at least one process is further configured to execute the computer-readable instructions to cause the wafer inspection apparatus to,
select a plurality of sample polar coordinates,
simulate a plurality of polar coordinate sets using the plurality of sample polar coordinates to find a plurality of polar coordinate sets, in which polar coordinates do not overlap one another,
calculate average values and deviations with regard to the found polar coordinate sets, and
derive the plurality of select polar coordinate sets, from among the found polar coordinate sets, using the average values and the deviations such that the plurality of select polar coordinate sets cover substantially an entire surface of the virtual wafer.

16. The wafer inspection apparatus of claim 13, wherein the at least one processor is further configured to execute the computer-readable instructions to cause the wafer inspection apparatus to derive a plurality of select polar coordinate sets by, deriving cartesian coordinate sets using the latin hypercube sampling, and converting the cartesian coordinate sets into the select polar coordinate sets.

17. The wafer inspection apparatus of claim 16, wherein the at least one processor is further configured to execute the computer-readable instructions to cause the wafer inspection apparatus to, select a plurality of sample cartesian coordinates, in consideration of a space and variables on the virtual wafer, simulate, using the sample cartesian coordinates, the cartesian coordinates to find a plurality of cartesian coordinate sets, in which cartesian coordinates do not overlap each other, obtain average values and deviations of result values of the found cartesian coordinates derived from the simulation; and derive, using the average value and deviation, a plurality of select cartesian coordinate sets such that the plurality of select cartesian coordinates cover substantially an entire surface of the virtual wafer.

* * * * *